United States Patent [19]
Martan et al.

[11] 4,124,643
[45] Nov. 7, 1978

[54] PREPARATION OF 3-FLUOROSALICYLALDEHYDE

[75] Inventors: Michael Martan, Rehovot, Israel; Dusan J. Engel, Des Plaines, Ill.

[73] Assignee: UOP Inc., Des Plaines, Ill.

[21] Appl. No.: 821,364

[22] Filed: Aug. 3, 1977

[51] Int. Cl.$^2$ ............................................. C07C 45/00
[52] U.S. Cl. ............................... 260/600 R; 568/775; 568/627; 568/656
[58] Field of Search ......................... 260/600 R, 623 R

[56] References Cited
U.S. PATENT DOCUMENTS 3,799,940  3/1974  Mains ............................ 260/600 R X
3,972,945  8/1976  Albright .......................... 260/600 R

OTHER PUBLICATIONS

Baldwin et al., Org. Reactions, vol. 22 (1975) pp. 10 and 11.

*Primary Examiner*—Bernard Helfin
*Attorney, Agent, or Firm*—James R. Hoatson, Jr.; Raymond H. Nelson; William H. Page, II

[57]  ABSTRACT

3-Fluorosalicylaldehyde may be prepared in a more economical manner by alkylating o-fluorophenol with an allyl halide such as allyl chloride, thereafter rearranging the resultant o-fluorophenyl allyl ether to form allyl-o-fluorophenol. The latter compound is then isomerized to form propenyl-o-fluorophenol. Thereafter this compound is subjected to ozonolysis at a subambient temperature to form the desired compound, namely, 3-fluorosalicylaldehyde.

3 Claims, No Drawings

PREPARATION OF 3-FLUOROSALICYLALDEHYDE

The invention herein described was made in the course of or under a contract or subcontract thereunder with the U.S. Air Force.

BACKGROUND OF THE INVENTION

With the advent of aircraft which are able to fly at relatively high speeds greater than Mach 1 plus the ability to climb to high altitudes it is necessary to provide an oxygen system which will perform under these relatively harsh conditions. This is especially true in the case of military aircraft which must possess the ability to fly higher, faster, longer and with greater maneuverability than other aircraft. In supplying an oxygen system for the cockpit of military aircraft, it is necessary to have a system which will perform in an adequate manner and which will be relatively light in weight. Another criteria is that the system be relatively small in size inasmuch as the cockpit area, especially in pursuit or fighter aircraft, is relatively small. One method of supplying oxygen to the personnel on the aircraft is to store oxygen as a liquid. One advantage in using such a system is that liquid oxygen does not require a high pressure tank and the ratio of system volume and weight versus the usable material could be drastically reduced. However, the disadvantage to the use of such a system is that expensive equipment is required on the ground in order to handle the problems of handling the cryogenic liquid.

As an alternative to using the relatively expensive liquid oxygen system, it has been found possible to concentrate oxygen use of the air and provide it to the aircraft crew members via certain metal chelates. One such metal chelate which has been found to be effective in the generation of oxygen from air is cobalt bis(3-fluorosalicylaldehyde) ethylene diimine which is known as fluomine. This cobalt chelate compound can reversibly bind oxygen and generate it by absorbing the oxygen at low temperatures and desorbing it at higher temperatures. For example, fluomine will absorb oxygen at a maximum rate between 80° and 100° F. while the desorption of the oxygen will take place above about 180° F. at relatively low pressures.

As a precursor to the formation of fluomine 3-fluorosalicylaldehyde is an important compound. Heretofore, this compound has been produced in various ways. The previous methods which have been used for the synthesis of 3-fluorosalicylaldehyde have been elaborate and resulted in the production of the desired compound at relatively low yields. For example, U.S. Pat. No. 3,780,110 describes a method in which o-fluorophenol is reacted with boron oxide caustic and a formaldehyde trimer known as trioxane in the presence of xylenes to effect an 80% conversion of the o-fluorophenol with a 22% selectivity to 3-fluorosalicylaldehyde and a 45% selectivity to 3-fluorosalicyl alcohol. In U.S. Pat. No. 3,855,305 it has been stated that an air oxidation of the 3-fluorosalicyl alcohol in the presence of p-toluidine will give a 58% yield of the desired compound, 3-fluorosalicylaldehyde. Thus, the combined amounts of the desired product which are produced represent a 38% yield of the desired product based upon the o-fluorophenol which is charged to the reaction. Other prior art methods as reported in the *American Perfumer And Aromatics*, Volume 69, page 31 or in the Chemical Reviews, Volume 60, page 169, disclose the use of the Reimer-Tiemann reaction for the direct method of converting phenols to hydroxybenzaldehydes. In the *Journal Of The American Chemical Society*, Volume 68, page 2502, a 39% conversion of o-fluorophenol with a 34% selectivity to 3-fluorosalicylaldehyde and a 39% selectivity to an isomer thereof has been reported. However, latter experiments were unable to reproduce this result, there being obtained only a 0-6% yield of the desired product.

Other workers have prepared o-fluorophenyl allyl ether in a 90.5-93% yield from o-fluorophenol and allyl bromide. Thereafter using a thermal Claisen rearrangement of the ether gave 6-allyl-2-fluorophenol in an 80% yield. However, attempts to oxidize this last named compound to 3-fluorosalicylaldehyde using dichromate solutions gave no reproducible results, i.e., a 55% yield from the first experiment but less than 5% in subsequent runs.

As will hereinafter be shown in greater detail, we have now discovered that relatively high yields of the desired product comprising 3-fluorosalicylaldehyde may be obtained when using a series of steps which constitute the present invention.

The invention relates to a novel process for the preparation of 3-fluorosalicylaldehyde. More specifically the invention is concerned with a process for preparing 3-fluorosalicylaldehyde using a series of steps involving alkylation, rearrangement, isomerization and ozonolysis whereby relatively large yields of the desired product may be obtained.

It is therefore an object of this invention to provide an improved process for obtaining 3-fluorosalicylaldehyde.

A further object of this invention is to provide a process for obtaining improved yields of 3-fluorosalicylaldehyde utilizing o-fluorophenol as a starting material.

In one aspect an embodiment of this invention resides in a process for the preparation of 3-fluorosalicylaldehyde which comprises the steps of: (a) condensing o-fluorophenol with an allyl halide at an elevated temperature; (b) rearranging the resultant o-fluorophenyl allyl ether at an elevated temperature to form allyl-o-fluorophenol; (c) isomerizing said allyl-o-fluorophenol in the presence of a catalyst containing a metal of Group VIII of the Periodic Table at an elevated temperature to form propenyl-o-fluorophenol; (d) subjecting said propenyl-o-fluorophenol to ozonolysis at a subambient temperature to form 3-fluorosalicylaldehyde; and (e) recovering the said 3-fluorosalicylaldehyde.

A specific embodiment of this invention is found in a process for the preparation of 3-fluorosalicylaldehyde which comprises condensing o-fluorophenol with allyl chloride at a temperature in the range of from about 25° to about 100° C., rearranging the resultant o-fluorophenyl allyl ether at a temperature in the range of from about 150° to about 250° C. to form allyl o-fluorophenol, isomerizing said o-fluorophenol in the presence of a catalyst comprising palladium composited on charcoal at a temperature in the range of from about 175° to about 225° C., thereafter subjecting the resultant propenyl-o-fluorophenol to ozonolysis in the presence of aqueous acetic acid at a temperature in the range of from about 0° to about 10° C. to form 3-fluorosalicylaldehyde and recovering the latter product.

Other objects and embodiments will be found in the following further detailed description of the present invention.

As hereinbefore set forth the present invention is concerned with a process for preparing 3-fluorosalicylaldehyde whereby greater yields of the desired product may be obtained. The process is effected in a series of four steps which comprise condensing or alkylating o-fluorophenol with an allyl halide, rearranging the resultant o-fluorophenyl allyl ether by means of a Claisen rearrangement reaction to form 6-allyl-2-fluorophenol, isomerizing the allyl-o-fluorophenol in the presence of certain catalytic compositions of matter hereinafter set forth in greater detail to form propenyl-o-fluorophenol and thereafter ozonizing this compound to form 3-fluorosalicylaldehyde.

The first step of the aforementioned process is effected by reacting o-fluorophenol with an allyl halide such as allyl chloride, allyl bromide, allyl iodide, allyl fluoride, the preferred allyl halide comprising allyl chloride due to its relative cost, at an elevated temperature in the presence of a basic material and a solvent. Examples of basic or alkaline materials which may be used will include sodium hydroxide, potassium hydroxide, lithium hydroxide, calcium hydroxide, magnesium hydroxide, sodium carbonate, potassium carbonate, lithium carbonate, magnesium carbonate, etc., while the solvents to be employed may include paraffins such as n-pentane, n-hexane, n-heptane, cyclopentane, cyclohexane, methylcyclopentane, etc., ketones such as acetone, methyl ethyl ketone, methyl propyl ketone, ethyl propyl ketone, dipropyl ketone, etc. The reaction is effected at elevated temperatures usually in the range of from about 25° to about 100° C. and at atmospheric pressure, although it is also contemplated within the scope of this invention that temperatures higher than those hereinbefore set forth may be employed if superatmospheric pressures ranging from 1 to about 100 atmospheres are also used.

Thereafter the o-fluorophenyl allyl ether which is thus formed is then rearranged in a Claisen type reaction whereby the ether is subjected to an elevated temperature ranging from about 150° to about 250° C. in the presence of an alkali compound and an antioxidant to form allyl-o-fluorophenol. If so desired, the reaction may be effected in the presence of solvents such as dimethylaniline, ethylpyridine, o-chlorophenol, benzonitrile, diphenyl ether, decalin, etc., although not necessarily with equivalent results. The thus formed allyl-o-fluorophenol is thereafter isomerized to form propenyl-o-fluorophenol. This isomerization is also effected at elevated temperatures ranging from about 175° to about 225° C. and in the presence of a catalyst. The catalyst which may be employed for this step of the process will comprise those compounds containing a metal of Group VIII of the Periodic Table and preferably a noble metal of Group VIII of the Periodic Table usually composited on a solid support. Some examples of these isomerization catalyst which may be employed will include palladium composited on activated charcoal, palladium composited on alumina, palladium composited on silica, platinum composited on activated charcoal, platinum composited on alumina, platinum composited on silica, rhodium composited on activated charcoal, rhodium composited on alumina, rhodium composited on silica, iridium composited on activated charcoal, iridium composited on alumina, iridium composited on silica, ruthenium composited on activated charcoal, ruthenium composited on alumina, ruthenium composited on silica, etc. If so desired, the catalyst which is employed may be pretreated with hydrogen and thereafter utilized to effect the isomerization. The thus formed propenyl-o-fluorophenol is thereafter subjected to ozonolysis to form the desired product, said ozonolysis reaction being effected at subambient temperatures ranging from about 0° to about 10° C. utilizing an aqueous acetic acid solution as the reaction medium. The ozonolysis is effected by passing an ozone-oxygen gas stream through the reaction mixture for a predetermined period of time and at a predetermined rate. Thereafter the desired product is recovered.

The process of this invention may be effected in any suitable manner and may comprise either a batch or continuous type of operation. For example, when a batch type operation is used, a quantity of the allyl halide and the o-fluorophenol along with the solvent and the alkaline compound may be placed in an appropriate apparatus such as an alkylation flask which is provided with stirring means and reflux means. The reaction mixture is heated to the desired operating temperature and maintained thereat for a period of time which may range from 0 to about 20 hours or more in duration. At the end of this time the apparatus and contents thereof are allowed to cool to room temperature and water is added to dissolve any solids which may be present. Thereafter the aqueous layer is separated from the organic layer and the former is extracted with a solvent such as benzene. The solvent is then combined with the product organic phase and subjected to distillation to remove the solvent. Thereafter the desired product comprising the o-fluorophenyl allyl ether is then recovered.

The o-fluorophenyl allyl ether is then placed in a second apparatus along with an alkali compound, an antioxidant, and, if so desired, a catalyst such as ammonium chloride, ammonium bromide, etc. Examples of alkali compounds which may be employed include sodium hydroxide, sodium carbonate, potassium hydroxide, potassium carbonate, etc.; while antioxidants which may be used will include compounds such as t-butylhydroxyanisole, etc. The apparatus is then heated to the desired operating temperature within the range hereinbefore set forth in greater detail and maintained thereat for a period which may again range from about 0.5 to about 20 hours or more in duration, the reaction mixture being maintained in a state of continuous agitation. Following this heating is discontinued and after the apparatus and contents thereof have cooled to room temperature the alkaline material is filtered off. The organic phase is then subjected to distillation to recover the allyl-o-fluorophenol. The allyl-o-fluorophenol which has been recovered is then charged to a third apparatus, along with a solvent such as diphenyl ether if so desired, and the catalyst comprising a compound containing a metal of Group VIII of the Periodic Table. The apparatus is then heated to the desired operating temperature and maintained thereat for a predetermined period while constantly stirring the reaction mixture. Upon completion of the reaction period, the apparatus is cooled and the solid catalyst may be removed by filtration. The filtrate is then subjected to fractional distillation to recover the isomerized product comprising propenyl-o-fluorophenol.

The propenyl-o-fluorophenol thus produced is then placed in an appropriate apparatus provided with stirring means, thermometer, a gas inlet and gas outlet and then cooled to a temperature ranging from about 0° to about 10° C., the cooling of said apparatus being accomplished by external means such as an ice bath. Upon reaching the desired temperature, a stream of ozone-oxygen is passed into the stirred reactants for a period of from about 1 to about 10 hours. Upon completion of the ozonolysis reaction, the solution is placed in a continuous liquid-liquid extractor containing water and extracted with an organic solvent such as benzene. After extraction, the organic phase is then washed with water, saturated with sodium chloride to remove the aqueous acetic acid and then with an aqueous sodium bicarbonate solution. The solvent is then removed from the aqueous phase by conventional means such as evaporation, vacuum, etc., and the desired product comprising 3-fluorosalicylaldehyde is recovered.

It is also contemplated within the scope of this invention that the desired product may be recovered utilizing a continuous method of operation. When this type of operation is employed, a quantity of the allyl halide and the o-fluorophenol are continuously charged to a reaction zone which is maintained at the proper operating conditions of temperature and pressure. In addition, the solvent and the alkaline material are also charged to the zone and after maintaining the reactants in said zone for a predetermined period of time, the reactor effluent is continuously withdrawn. The effluent is subjected to conventional means of separation whereby any unreacted starting materials, solvent and alkaline compound are recovered for recycle to the reaction zone while the o-fluorophenyl allyl ether is continuously charged to a second reaction zone which is maintained at the proper operating conditions of temperature and pressure and which also contains an alkaline compound. After passage through this zone, the reactor effluent which has undergone rearrangement is continuously withdrawn and separated from the alkaline compound as well as any unreacted o-fluorophenyl allyl ether. The latter is recycled to the second reaction zone while the allyl-o-fluorophenol is continuously charged to a third reaction zone which contains the catalyst and a solvent, if so desired. After passage over the catalyst and through the isomerization zone, the isomerized propenyl-o-fluorophenol is continuously withdrawn and after separation from any unreacted starting materials is passed to a fourth reaction zone wherein it is subjected to ozonolysis by treatment with an oxygen-ozone stream. If so desired, the aqueous acetic acid may be admixed with the propenyl-o-fluorophenol prior to entry into the ozonolysis zone and charged thereto in a single stream. As hereinbefore set forth the ozonolysis zone is maintained at subambient temperatures ranging from about 0° up to about 10° C. After passage through this zone, the reactor effluent is continuously withdrawn and treated in a manner similar to that hereinbefore set forth whereby the desired 3-fluorosalicylaldehyde may be separated and recovered.

The following examples are given for purposes of illustrating the process of the present invention. However, it is to be understood that these examples are given merely for purposes of illustration and that the present invention is not necessarily limited thereto.

EXAMPLE I

In this example 1325 grams (18.4 mole) of methyl ethyl ketone and 738 grams (5.34 mole) of finely ground anhydrous potassium carbonate were stirred together in a nitrogen blanketed 3-liter round bottom flask which was equipped with a mechanical stirrer, reflux condenser and a thermometer which extended into the reactants. Thereafter 600 grams (5.35 mole) of o-fluorophenol was added to the mixture following which the temperature rose to 52° C. The contents of the flask were then heated to 82° C. (reflux temperature) and 410 grams (5.35 mole) of allyl chloride was added during a period of 45 minutes. During this time the reflux temperature dropped to 77° C. Heating was continued in order to maintain a vigorous reflux along with constant stirring for a period of 8.5 hours. At the end of this time, the reflux temperature was 85° C. and a gas chromatographic analysis indicated that there had been an 88% conversion of the o-fluorophenol.

The contents of the flask were allowed to cool to room temperature and 2 liters of water were added to dissolve the solids which were present in the mixture. The aqueous layer was separated and extracted with benzene. The benzene was stripped from the extracts and the residue was combined with the organic phase of the product. Thereafter the methyl ethyl ketone was distilled off and the residue transferred to an Oldershaw distillation column. The mixture was distilled and 123 grams of distillate was obtained, the main component of the distillate being unreacted o-fluorophenol. The slightly dark colored residue was subjected to additional distillation under reduced pressure and 624 grams (4.11 mole) of o-fluorophenyl allyl ether which had a boiling point of 86.5–87.5° C. at 18 torr was recovered. It was determined that there had been an 80% conversion of the o-fluorophenol with a 96% selectivity to the ether. To rearrange the ether, 300 grams (1.97 mole) of the o-fluorophenyl allyl ether along with 6.0 grams of t-butylhydroxyanisole and 1.8 grams of anhydrous sodium carbonate were placed in a nitrogen blanketed flask equipped with a mechanical stirrer, reflux condenser and thermometer. The contents of the flask were stirred while heating to a temperature of 190° C. in a wax bath for a period of 1 hour. The temperature of the reaction was maintained for an additional period of 6.5 hours, after which the flask and contents thereof were cooled to room temperature under a continuing nitrogen blanket. The sodium carbonate was filtered off and the remainder subjected to distillation through an Oldershaw column. There was recovered 248 grams of distillate which contained 220 grams of allyl-o-fluorophenol.

Analysis disclosed that there had been a 98.5% conversion of the ether with a 79% selectivity to the allyl-o-fluorophenol.

Isomerization of the allyl-o-fluorophenol was accomplished by placing 720 grams of diphenyl ether, 467 grams of allyl-o-fluorophenol and 5 grams of a catalyst comprising 5% palladium on charcoal in a 2 liter round bottom flask provided with stirring means, reflux means and thermometer. The flask was purged with nitrogen and stirring was initiated after the flask was immersed in an 80° C. wax bath. Following this, the reactants were heated to a temperature of 195° C. and maintained thereat for a period of 5 hours. After cooling the solid catalyst was filtered and the filtrate was distilled through the Oldershaw column. Analysis disclosed that there had been a 97% conversion of the allyl-o-fluorophenol with a 94% selectivity to propenyl-o-fluorophenol.

To effect the desired ozonolysis, 87 grams of the propenyl-o-fluorophenol which was prepared above along with 600 grams of glacial acetic acid and 75 grams of water were placed in a 1 liter round bottom flask equipped with a mechanical stirrer, thermometer, gas inlet through a sintered glass sparger and a gas outlet leading to a scrubber containing 400 cc of 2% potassium iodide solution and then to a wet test gas meter. The contents of the flask were cooled to 0° C. under a nitrogen blanket following which an ozone-oxygen gas stream was passed into the stirred reactants at a rate of 8 cubic feet per hour. The stream was generated by passing oxygen through an ozonator so that the stream contained 1.2% ozone. After a period of 5.5 hours, the scrubber containing the potassium iodide solution turned dark due to the ozone oxidation of iodide to iodine thus indicating that the reactants were no longer absorbing ozone. The ozonized solution was transferred to a liquid/liquid extractor containing 1200 cc of water and was extracted for a period of 16 hours with 2.5 liters of benzene. Upon completion of the extraction, the aqueous phase was discarded and the organic phase was washed with a total of 2 liters of benzene. The organic phase was then washed with a total of 2 liters of water which had been saturated with sodium chloride in order to remove the acetic acid and then with 250 cc of a 4% aqueous sodium bicarbonate solution which was also saturated with sodium chloride. The benzene was evaporated on a rotary evaporator to give 70 grams of crude 3-fluorosalicylaldehyde.

The crude 3-fluorosalicylaldehyde was combined with 1800 cc of deionized water, the contents were stirred and azeotropically distilled at a temperature of 97° C. By maintaining the condenser at a temperature of 70° C. the 3-fluorosalicylaldehyde was maintained in liquid state. Upon completion of the distillation, the distillate was cooled in ice and the 3-fluorosalicylaldehyde was separated from the aqueous distillate. The solids were broken up and mixed with 700 cc of water and 2800 cc of methanol at a temperature of 70° C. to obtain a uniform solution. A slow cooling of the solution resulted in the obtention of fluffy crystals of 3-fluorosalicylaldehyde which were filtered off. The crystals were dissolved in hexane, the hexane being present in a ratio of 4:1 of hexane to 3-fluorosalicylaldehyde, the water which separated was removed and the hexane was cooled to 0° C. to recover dry 3-fluorosalicylaldehyde. The 3-fluorosalicylaldehyde had a melting point of 67°-69° C., gas chromatography indicating a 100% purity. There had been a 100% conversion of propenyl-o-fluorophenol with an 87% selectivity to the 3-fluorosalicylaldehyde.

EXAMPLE II

When the above experiment was repeated using 147.6 grams of allyl bromide in place of the allyl chloride in the alkylation of o-fluorophenol there was obtained a 95% conversion of the o-fluorophenol with a 96% selectivity to o-fluorophenyl allyl ether.

The ether was rearranged at temperature ranging from 190°-195° C. using ammonium chloride, ammonium bromide, as catalysts. In the first case, there as a 68% conversion of the ether in 3 hours with an 87% selectivity to allylfluorophenol, the ratio of ortho to para isomer being 6:1. In the second instance there was a 79% conversion with a 86% selectivity.

Isomerization of the allyl-o-fluorophenol was effected in a manner similar to that set forth in Example I above using a 5% rhodium on charcoal catalyst in place of the palladium on charcoal catalyst. The isomerization was effected at a temperature of about 200° C. for a period of about 2 hours, there being obtained a 79% conversion of the allyl-o-fluorophenol with a 95% selectivity to propenyl-o-fluorophenol.

Ozonolysis of this product in a manner similar to that set forth in Example I above again gave a 100% conversion of the propenyl-o-fluorophenol with an 86% selectivity to 3-fluorosalicylaldehyde.

We claim as our invention:

1. A process for the preparation of 3-fluorosalicylaldehyde which comprises the steps of:
   (a) isomerizing allyl-o-fluorophenol in the presence of a catalyst containing a metal of Group VIII of the Periodic Table at a temperature of from about 175° to about 225° C. to form propenyl-o-fluorophenol;
   (b) subjecting said propenyl-o-fluorophenol to ozonolysis at a temperature of from about 0° to about 10° C. in the presence of aqueous acetic acid to form 3-fluorosalicylaldehyde; and
   (c) recovering said 3-fluorosalicylaldehyde.

2. The process as set forth in claim 1 in which said catalyst is palladium composited on charcoal.

3. The process as set forth in claim 1 in which said catalyst is rhodium composited on charcoal.

* * * * *